United States Patent
Loui et al.

(10) Patent No.: US 8,762,075 B2
(45) Date of Patent: Jun. 24, 2014

(54) MICROCANTILEVER-BASED GAS SENSOR EMPLOYING TWO SIMULTANEOUS PHYSICAL SENSING MODES

(75) Inventors: Albert Loui, Dublin, CA (US); Donald J. Sirbuly, Encinitas, CA (US); Selim Elhadj, Livermore, CA (US); Scott K. McCall, Livermore, CA (US); Bradley R. Hart, Arlington, VA (US); Timothy V. Ratto, Oakland, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 688 days.

(21) Appl. No.: 12/852,416

(22) Filed: Aug. 6, 2010

(65) Prior Publication Data
US 2011/0077872 A1 Mar. 31, 2011

Related U.S. Application Data

(60) Provisional application No. 61/246,866, filed on Sep. 29, 2009.

(51) Int. Cl.
*G01N 31/00* (2006.01)

(52) U.S. Cl.
USPC .......................................................... 702/24

(58) Field of Classification Search
USPC ........... 702/24, 30, 42, 45, 47, 50, 53, 54, 56, 702/57, 75, 100, 130, 132, 133, 162, 168
See application file for complete search history.

(56) References Cited

U.S. PATENT DOCUMENTS

| | | |
|---|---|---|
| 3,768,301 A | 10/1973 | Feichtinger |
| 4,080,821 A | 3/1978 | Johnston |
| 4,164,862 A | 8/1979 | Jackson |
| 4,314,242 A | 2/1982 | Kuru et al. |
| 4,549,427 A | 10/1985 | Kolesar, Jr. |
| 4,706,061 A | 11/1987 | Johnson |
| 5,339,675 A | 8/1994 | DiLeo et al. |
| 5,345,815 A | 9/1994 | Albrecht et al. |
| 5,445,008 A | 8/1995 | Wachter et al. |
| 5,719,324 A | 2/1998 | Thundat et al. |
| 5,750,989 A * | 5/1998 | Lindsay et al. ................. 850/14 |
| 5,756,878 A | 5/1998 | Muto et al. |

(Continued)

OTHER PUBLICATIONS

Xu et al., Viscous damping of microresonators for gas composition analysis, 2006, American institute of Physics, pp. 143513-1 to 143513-2.*

(Continued)

*Primary Examiner* — Mohamed Charioui
(74) *Attorney, Agent, or Firm* — Domininc M. Kotab

(57) ABSTRACT

According to one embodiment, a system for detecting and identifying gases includes a piezoresistive microcantilever transducer, wherein dissipation of heat from the piezoresistive microcantilever into one or more gases is measured by changes in an electrical resistance of the piezoresistor, a vibrating microcantilever transducer, wherein shifts are measured in resonant frequency of the vibrating microcantilever due to viscous damping thereof by the one or more gases, and a subsystem for correlating the measured resistance changes and the resonant frequency shifts to the one or more gases. In another embodiment, a method for detecting and identifying one or more gases includes determining dissipation of heat from a microcantilever into one or more gases, and determining shifts in resonant frequency of the microcantilever due to viscous damping thereof by the one or more gases. Other systems, methods, and computer program products are also described according to more embodiments.

20 Claims, 6 Drawing Sheets

(56) References Cited

U.S. PATENT DOCUMENTS

| | | | |
|---|---|---|---|
| 5,756,881 A * | 5/1998 | Stockli et al. | 73/40.7 |
| 5,918,263 A * | 6/1999 | Thundat | 73/35.16 |
| 6,041,642 A | 3/2000 | Duncan | |
| 7,555,938 B2 * | 7/2009 | Bargatin et al. | 73/64.53 |
| 7,634,937 B2 | 12/2009 | Burdett et al. | |
| 2005/0180864 A1 * | 8/2005 | Ursan et al. | 417/390 |
| 2005/0199047 A1 * | 9/2005 | Adams et al. | 73/105 |
| 2008/0085212 A1 * | 4/2008 | Adams et al. | 422/50 |
| 2010/0095745 A1 * | 4/2010 | Flynn et al. | 73/40.7 |
| 2010/0116024 A1 * | 5/2010 | De Coulon et al. | 73/25.03 |
| 2011/0302996 A1 * | 12/2011 | Djakov et al. | 73/54.01 |

OTHER PUBLICATIONS

S. Tetin et al., "Modeling and performance of uncoated microcantilever-based chemical sensors," © 2009 Elsevier B.V., Sensors and Actuators B: Chemical, vol. 143 (2010) p. 555-560.

A. Loui et al., "Detection and discrimation of pure gases and binary mixtures using a dual-modality microcantilever sensor," © 2010 Elsevier, Sensors and Actuators A: Physical, vol. 159 (2010) p. 58-63.

A. Loui et al., "An analytic model of thermal drift in piezoresistive microcantilever sensors," © 2010 American Institute of Physics, Journal of Applied Physics, vol. 107, (2010) 054508, p. 1-13.

W. H. King "Piezoelectric Sorption Detector," Journal of Analytical Chem., vol. 36, No. 9, Aug. 1964, p. 1735-1739.

F.R. Blom et al., "Dependence of the quality factor on micromachined silicon beam resonators on pressure and geometry," © American Vacuum Society, Journal of Vacuum Science, Technol. B 10 (1), Jan./Feb. 1992, p. 19-26.

J.W. Grate, "Acoustic wave microsensor arrays for vapor sensing," © 2000 American Chemical Society, Chem. Rev. 2000, vol. 100, p. 2627-2648.

I. Simon et al., "Thermal and gas-sensing properties of a micromachined thermal conductivity sensor for the detection of hydrogen in automotive applications," © 2002 Elsevier Science B.V., Sensors and Actuators A, 97-98 (2001), p. 104-108.

C. Ducso et al., "Explosion-proof monitoring of hydrocarbons by mechanically stabilised, integrable calorimetric microsensors," © Elsevier Science B.V., Sensors and Actuators B. 95 (2003) p. 189-194.

P. Tardy et al., "Dynamic thermal conductivity sensor for gas detection," © 2003 Elsevier B.V., Sensors and Actuators B 98 (2004) p. 63-68.

Y. Xu et al., "Viscous damping of microresonators for gas composition analysis," © 2006 American Institute of Physics, Applied Physics Letters, 88 (2006) Art No. 143513, p. 1-3.

K.J. Kim et al., "Thermal Conduction between a heated microcantilever and a surrounding air environment," © 2008 Elsevier Ltd., Applied Thermal Engineering, vol. 29 (2009) p. 1631-1641.

* cited by examiner

MICROCANTILEVER-BASED GAS SENSOR EMPLOYING TWO SIMULTANEOUS PHYSICAL SENSING MODES

The United States Government has rights in this invention pursuant to Contract No. DE-AC52-07NA27344 between the United States Department of Energy and Lawrence Livermore National Security, LLC for the operation of Lawrence Livermore National Laboratory.

RELATED APPLICATIONS

The present application claims priority to a U.S. Provisional Patent Application filed Sep. 29, 2009, under Appl. No. 61/246,866, which is incorporated herein by reference.

FIELD OF THE INVENTION

The present invention relates to the detection of gases, and more particularly, to the selective detection of gases using a microcantilever-based gas sensor employing two simultaneous physical sensing modes.

BACKGROUND

Piezoresistive microcantilevers have been widely used in micro-electro-mechanical systems (MEMS) sensor arrays for the detection of chemical vapors and gases, where the embedded signal transducer (the piezoresistor) provides a more compact, rugged, and low-power alternative to the optical feedback mechanisms inherited from atomic force microscopy.

It is well known in the art, particularly with respect to chromatographic analysis of gas flows, that a gas or simple mixture of gases (e.g., a binary mixture, a ternary mixture, etc.) can be identified by measuring the gas' thermal conductivity. This is typically achieved by placing a resistance temperature detector ("RTD"), a thermocouple, etc., in the gas to be identified. In order to measure the electrical resistance of the RTD, a small amount of power is supplied which causes the RTD temperature to be greater than the gas temperature. As a result of the temperature difference between the RTD and the surrounding gas, the electrical power delivered to the RTD is dissipated into the gas as heat. If the gas composition changes (for example, goes from 100% nitrogen to 95% nitrogen/5% argon), the thermal conductivity of the gas also changes. The result is a change in heat dissipation efficiency of the RTD, with an increase/decrease of heat dissipation leading to a decrease/increase, respectively, in RTD temperature, under constant power conditions. The prior art teaches a typical strategy, in which the electrical power is adjusted in a feedback mechanism to maintain a constant RTD temperature. Alternatively, the power can be kept constant, and the RTD temperature allowed to fluctuate freely with changes in gas composition. Since the RTD has a large temperature coefficient of resistance (e.g., approximately 4000 ppm/K, for a platinum resistance thermometer), the change in temperature with gas composition leads to a change in resistance that is readily measured by a Wheatstone bridge circuit.

In typical thermal conductivity sensor designs, the sensor power is continuously varied to keep the sensor temperature constant, requiring an active temperature feedback control mechanism. This design has some limitations, particularly regarding response time to thermal conductivity changes.

A similar apparatus disclosed in the prior art is used to determine gas flow rate. As will be described below, the RTD temperature varies with the following gas properties: 1) thermal conductivity, 2) temperature, and 3) flow rate. A Wheatstone bridge configuration may be used with several RTDs arranged such that the thermal effects are substantially eliminated, and only variations of flow rate affect the RTD temperature.

In other prior art, a mechanical vibration of a rigid body in a fluid (gas or liquid) has been exploited as a diagnostic and scientific tool. The vibrating body ("oscillator"), typically driven to bulk oscillation by a piezoelectric element, possesses intrinsic resonant frequencies that are altered upon interaction with certain external influences. This operating concept is prototypically embodied in the quartz crystal microbalance (QCM), where the addition of mass to the oscillator causes a shift in the resonant frequencies that are detected. Typically, the fundamental or a low harmonic frequency is monitored. Such a device is well known in the art of thin film deposition, where they are often referred to as thickness monitors. Furthermore, gas and chemical vapor detection is enabled with the addition of coatings to which the gas-phase species have some tendency to bind. This approach has since been widely applied to QCM devices for sensing applications. Devices based on the propagation of surface acoustic waves (SAW), as opposed to the bulk acoustic waves that exist in a QCM, have also become widely investigated as sensors. The use of vibrating coated microcantilevers for chemical vapor detection exists in the prior art.

However, the selection of detector coatings for gases at typical temperature and pressure conditions of interest (e.g., ambient, atmospheric) is often problematic. First, many gases under such conditions have little thermodynamic tendency to partition into the bulk of common sensing materials (e.g., polymers). This is the result of low cohesive energy densities and hence small solubility parameters, particularly for non-polar gases. Second, since chemisorptive interactions are usually exploited as a means of detecting and identifying gas-phase analytes, highly inert species, such as $N_2$ and noble gases, are virtually undetectable by sensors using chemically functionalized materials (e.g., alkanethiol self-assembled monolayers). In the absence of such coatings, the sorption tendencies of the oscillator surface are low (i.e., zero/near-zero sticking coefficient) at or near ambient atmospheric pressures due to the persistent saturation coverage of up to a few mono-layers of adsorbed gases such as oxygen and carbon monoxide. Therefore, the mechanism of frequency shift due to mass addition to the oscillator is inappropriate for non-reactive gases such as $N_2$ and noble gases.

None of the teachings heretofore available in the prior art provide a method of selective gas detection which allows: 1) that gases are detected at concentrations of interest (e.g., parts-per-million); and 2) that gases are mutually distinguished from one another, whether they occur individually or simultaneously in a mixture. Gas sensors that are based on the heat conduction process described above suffer from non-unique responses, since many pure gases (or mixtures thereof) may have the same thermal conductivity. Similarly, gas sensors based on resonant frequency shifts are limited by the nonuniqueness of viscosity and density amongst possible gas analytes. Therefore, a gas sensor which is capable of overcoming the different problems associated with sensors using the dissimilar physical mechanisms of gas sensing described above would aid greatly in selective gas detection.

SUMMARY

In one embodiment, a system for detecting and identifying gases includes a piezoresistive microcantilever transducer, wherein dissipation of heat from the piezoresistive microcantilever into one or more gases is measured by changes in an electrical resistance of the piezoresistor, a vibrating microcantilever transducer, wherein shifts are measured in resonant frequency of the vibrating microcantilever due to viscous damping thereof by the one or more gases, and a subsystem for correlating the measured resistance changes and the resonant frequency shifts to the one or more gases.

In another embodiment, a method for detecting and identifying one or more gases includes determining dissipation of heat from a microcantilever into one or more gases, and determining shifts in resonant frequency of the microcantilever due to viscous damping thereof by the one or more gases.

In yet another embodiment, a computer program product for detecting and identifying one or more gases includes a computer readable medium having computer readable program code embedded therein. The computer readable program code is configured to: receive data regarding changes in an electrical resistance of a piezoresistor; receive data regarding shifts in resonant frequency of a microcantilever; determine dissipation of heat from the microcantilever into one or more gases based on the data regarding changes in the electrical resistance of the piezoresistor; determine viscous damping of the one or more gases based on the data regarding shifts in resonant frequency of the microcantilever; correlate the dissipation of heat and the viscous damping to one or more gases; and output the identity of the one or more gases based on the correlation.

Other aspects and embodiments of the present invention will become apparent from the following detailed description, which, when taken in conjunction with the drawings, illustrate by way of example the principles of the invention.

DETAILED DESCRIPTION

Figure 1:
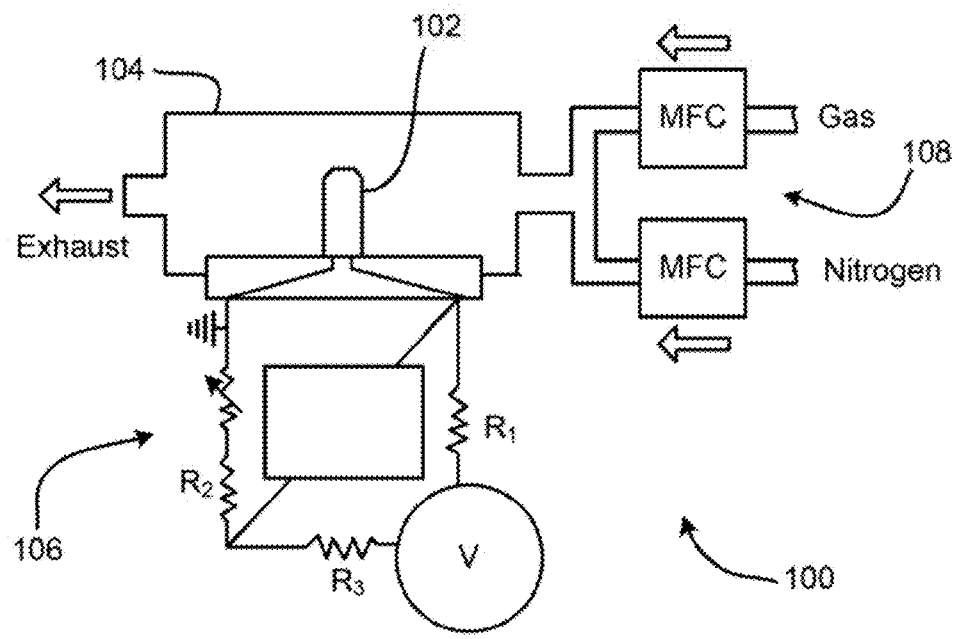
FIG. 1 shows a schematic overview of an experimental apparatus for measuring gas properties, according to one embodiment.

The following description is made for the purpose of illustrating the general principles of the present invention and is not meant to limit the inventive concepts claimed herein. Further, particular features described herein can be used in combination with other described features in each of the various possible combinations and permutations.

Unless otherwise specifically defined herein, all terms are to be given their broadest possible interpretation including meanings implied from the specification as well as meanings understood by those skilled in the art and/or as defined in dictionaries, treatises, etc.

It must also be noted that, as used in the specification and the appended claims, the singular forms "a," "an" and "the" include plural referents unless otherwise specified.

In one general embodiment, a system for detecting and identifying gases includes a piezoresistive microcantilever transducer, wherein dissipation of heat from the piezoresistive microcantilever into one or more gases is measured by changes in an electrical resistance of the piezoresistor, a vibrating microcantilever transducer, wherein shifts are measured in resonant frequency of the vibrating microcantilever due to viscous damping thereof by the one or more gases, and a subsystem for correlating the measured resistance changes and the resonant frequency shifts to the one or more gases.

In another general embodiment, a method for detecting and identifying one or more gases includes determining dissipation of heat from a microcantilever into one or more gases, and determining shifts in resonant frequency of the microcantilever due to viscous damping thereof by the one or more gases.

In yet another general embodiment, a computer program product for detecting and identifying one or more gases includes a computer readable medium having computer readable program code embedded therein. The computer readable program code is configured to: receive data regarding changes in an electrical resistance of a piezoresistor; receive data regarding shifts in resonant frequency of a microcantilever; determine dissipation of heat from the microcantilever into one or more gases based on the data regarding changes in the electrical resistance of the piezoresistor; determine viscous damping of the one or more gases based on the data regarding shifts in resonant frequency of the microcantilever; correlate the dissipation of heat and the viscous damping to one or more gases; and output the identity of the one or more gases based on the correlation.

According to one embodiment, a method for detecting and identifying pure gases and binary gas mixtures includes a novel correlation of two distinct physical mechanisms based on readings from a pair of microcantilever transducers. The physical mechanisms (methods of detecting and identifying) are 1) heat dissipation, and 2) resonant damping in the viscous regime, according to two approaches. The first method involves characteristic dissipation of heat into the sample gas by an RTD, thermocouple, etc. The efficiency of heat dissipation varies with the gas thermal conductivity, temperature, and flow rate, and is measured directly by changes in the electrical resistance of the RTD, according to one embodiment. The second method, in one approach, relies on characteristic shifts in resonant frequency of a vibrating microcantilever resulting from viscous damping in the sample gas. These frequency shifts depend on the viscosity and density of the sample gas. The simultaneous operation of these two microcantilever-based sensing modalities, in most embodiments, yields uniquely identifying signatures for sample gases that cannot otherwise be obtained from detection methods using similar physical principles individually.

In one embodiment, the RTD may be a silicon microcantilever with an embedded piezoresistor. The RTD may be wired serially to a surface mount resistor to form one voltage divider leg of a Wheatstone bridge circuit, in one approach. A potentiometer may be wired serially to another surface mount resistor that comprises the other voltage divider leg of the Wheatstone bridge circuit. Either a direct current (DC) or alternating current (AC) source voltage is applied to the parallel voltage divider legs to enact detection. The bridge voltage is measured by a differential amplifier across the midpoint of each voltage divider. The temperature coefficient of resistance is significantly larger for the piezoresistor compared to the other resistor components in the bridge (for example, 3000 ppm/K compared with about 50 ppm/K). Therefore, the embedded piezoresistor is the only element within the bridge circuit that experiences a significant, detectable change in resistance upon exposure to gases of changing thermal conductivity which signals a changing composition. The circuit elements other than the RTD may also be isolated from the sampled gas by enclosure in a hermetically-sealed case, further reducing the contributions of these non-RTD components to the detection response.

According to one approach, a passive sensing strategy may be used where the power supplied to the piezoresistor is kept constant such that the temperature and hence electrical resistance changes in response to the variations in the gas composition. In typical thermal conductivity sensor designs, the sensor power is continuously varied to keep the sensor temperature constant, requiring an active temperature feedback control mechanism. The use of a passive sensing strategy eliminates this need, and the absence of delays between the measurement and adjustment of sensor temperature permits a faster response time.

Some typical flow sensors use temperature variations in the sensor to determine flow changes in a gas of fixed composition. In these arrangements, the sensor temperature varies with the following gas properties: 1) thermal conductivity, 2) temperature, and 3) flow rate. A Wheatstone bridge configuration may be used with several resistance temperature detectors arranged such that the thermal effects are substantially eliminated, and only variations of flow rate affect the sensor temperature.

According to some approaches, however, the opposite result is desired. The detection and identification of gases dictates that only variations of the thermal conductivity affect the sensor temperature, and the effect of gas temperature and flow rate should be substantially eliminated for the sensor to work properly.

Gas flow variations in proximity to the RTD create errors in the determination of the gas identity. One assumption used in the sensor design, according to one embodiment, is that variations in the temperature of the RTD are directly and solely correlated to variations in the thermal conductivity (k) of the gas. Since the thermal conductivity provides an indication of the gas identity, the measurement of the temperature variation by the RTD provides a method for deducing the gas composition (and changes thereof). However, the RTD temperature is determined by the overall dissipation of electrical power by the RTD into the gas in the form of heat. The heat dissipation, in principle, occurs through several mechanisms: 1) heat conduction, which depends on both the gas thermal conductivity and gas temperature; 2) heat loss by both buoyancy-driven ("free") and flow-driven ("forced") convection, which depends on not only gas thermal conductivity and gas temperature but, in the latter case, the flow rate of the gas; and 3) heat loss by radiation, which depends on the relative temperatures of the RTD and the gas.

For typical operational temperatures of the RTD, according to one embodiment about 300K-320K, which corresponds to a low power input (about 1 mW), heat dissipation by radiation is negligible. Also, free convection is not a significant mechanism of heat loss for a heated microcantilever in a gaseous medium under conditions where continuum fluid mechanics are applicable (i.e., at pressures greater than about 1 Torr). Therefore, heat dissipation is affected by both heat conduction and forced convection, and variations in the following gas properties will cause a temperature change in the RTD: 1) thermal conductivity; 2) temperature; and 3) gas flow rate, according to preferred embodiments. Near ambient atmospheric conditions, the thermal conductivity is substantially constant with respect to temperature and pressure.

Instead of using a multi-inlet, perpendicular gas flow cell to mitigate the effect of gas flow variations, as described in the prior art, a small pump may be used, according to one approach, to maintain a constant gas sampling flow rate of approximately 10 standard cubic centimeters per minute (sccm), or a freestream flow speed of approximately 5 centimeters per second. The pump may have a low compression ratio in order to ensure that there are no substantial differences in flow rate between gases of different composition. While this strategy does not eliminate heat loss due to forced convection, it ensures that any measured variations in RTD temperature are due only to changes in gas thermal conductivity and/or temperature. Then, under isothermal conditions of operation, the RTD temperature becomes exclusively correlated to the thermal conductivity of the gas. For operation at temperatures and pressures substantially greater than those present in ambient atmospheric conditions (e.g., an order of magnitude or more), the effect of temperature and pressure variations on the gas thermal conductivity may also be assessed. In this case, separate temperature and pressure detectors placed in the gas and in proximity to the RTD can measure and track the variations in the gas temperature and pressure, in some approaches. This information can then be used to compensate for the effect of temperature and pressure variations on the temperature of the RTD, using semi-empirical and analytic models known in the art.

The vibrating microcantilever will experience a frequency shift that depends on the following gas properties: 1) viscosity; and 2) density, in some approaches. It is known in the art that gas viscosity and density are generally functions of temperature and pressure, and that the viscosity is substantially constant with respect to pressure near ambient atmospheric conditions. The detection and identification of gases dictate that only changes in viscosity and density affect the oscillator frequency, and that variations thereof with respect to temperature and pressure are substantially eliminated. For operation at temperatures and pressures substantially greater than those present in ambient atmospheric conditions (e.g., an order of magnitude or more), the effect of temperature and pressure variations on the gas viscosity and density may also be assessed. In this case, separate temperature and pressure detectors placed in the gas and in proximity to the sensor can measure and track the variations in the gas temperature and pressure, in some approaches. This information can then be used to compensate for the effect of temperature and pressure variations on the temperature of the sensor, using semi-empirical and analytic models known in the art.

In one embodiment, the combination of both a heat conduction and a resonant frequency shift detection method yields uniquely identifiable signatures for sample gases that cannot otherwise be obtained from the detection methods individually. According to one embodiment, selectivity may be a product of the dissimilar physical mechanisms of gas sensing: 1) heat conduction, which depends on the gas thermal conductivity, temperature, and flow rate; and 2) resonant frequency shift due to viscous damping, which depends on the gas viscosity and density. The microcantilever serves as a common platform for these two transduction modes of gas sensing, according to one approach. Since both the thermal conductivity and viscosity of the gas are different functions of temperature (approximately proportional to $T^{1/2}$ and $T^{3/2}$, respectively), the optional creation of parallel gas flow circuits operating at different gas temperatures creates additional operating mode(s) to enhance selectivity. This combined method allows for the selective detection of a wide range of gases including hydrogen, methane, carbon dioxide, and noble gases, in preferred embodiments.

EXPERIMENTS

Gas sensing experiments were performed using a hand-portable, piezoresistive microcantilever array sensor previously developed for the detection of chemical vapors, including chemical warfare agents. In the study, gases were identified based on their thermal conductivity rather than on their potential chemical bonding properties, so microcantilevers devoid of functional polymeric coatings—and hence operationally identical—were utilized. The piezoresistance signals from eight microcantilever channels were measured to ensure full redundancy in the sensor response. A schematic diagram of the circuit is shown in FIG. 1.

Eight representative gases were selected to demonstrate the heat dissipation sensing concept, along with $N_2$ as a common diluent in binary mixtures. These ultrahigh purity gases were purchased commercially from various sources, including: Air Liquide America (Houston, Tex., USA), Matheson Tri-Gas (Parsippany, N.J., USA), Airco (Santa Clara, Calif., USA), Air Products (Allentown, Pa., USA), and Airgas (Radnor, Pa., USA).

A system 100 was used to prepare the binary gas mixtures with $N_2$, as shown in FIG. 1. The system 100 included a gas sensor which comprised a Wheatstone circuit 106 and a gas flow cell 104, a gas mixing system 108 having two mass flow controllers (MFC), and a microcantilever 102 (of which there were 8, but only one is shown in FIG. 1). Concentrations of each gas mixture between 0% (pure $N_2$) and 100% (pure gas) were obtained by simple two-channel mixing based on relative flow rates. Gas temperatures were measured by a K-type thermocouple inserted into the mixed gas flow approximately 15 cm upstream of the sensor inlet. Total flow rates between 18 sccm and 90 sccm were measured downstream of the sensor exhaust outlet using an ADM2000 flow meter from Agilent Technologies (Santa Clara, Calif., USA). All experiments were conducted at ambient atmospheric pressure, about 14.7 pounds per square inch, absolute.

Thermal conductivity based sensing was performed using the system 100. The basic sensing principle involving heat dissipation, as embodied by a piezoresistive microcantilever, is simple: as the gaseous environment becomes more or less conductive to heat, the electrically-powered "self-heated" piezoresistor decreases or increases its temperature, respectively. Since the piezoresistor is a doped semiconductor, its resistance $R_c$ depends on its temperature $T_c$ in a characteristic manner. Therefore, measurement of $R_c$ provides information about the thermal conductivity of the gas, and can then be used to determine the identity of the gas.

A closed form model to describe the thermal response behavior of piezoresistive microcantilevers in gaseous environments with potentially varying thermal conductivity, temperature, and flow rate successfully predicted the thermal drift in field data obtained with the microcantilever array sensor described. In the prior work, calculations revealed that the piezoresistive response $\Delta R_c/R_c$ to gases in a constant temperature environment was dominated by thermal conductivity changes, with concomitant bending contributions induced by changes in $T_c$ nearly three orders of magnitude smaller. Although changing environmental temperatures will create additional contributions to $\Delta R_c/R_c$ independently of the gaseous thermal conductivity, these effects can be ignored in the present study as a result of the isothermal experimental conditions.

The thermal conductivities (mW/m·K) of various gases at 298K that were examined are listed in Table 1. For the piezoresistive microcantilevers employed in this work, the boron dopant is implanted at an approximate dose of $5\times10^{15}$ cm$^{-2}$. This dopant level is sufficiently high that hole-phonon scattering dominates over the effect of increased carrier concentration from thermal promotion to the conduction band. Thus, the overall effect is an increase in resistance with an increase in temperature (i.e., a positive temperature coefficient of resistance), with a high degree of linearity in a range of about 250K to about 800K.

TABLE 1

| Gas | Thermal Conductivity (mW/m · K) |
| --- | --- |
| Xe | 5.65 |
| Kr | 9.43 |
| $CO_2$ | 16.9 |
| Ar | 17.7 |
| $N_2$ | 25.8 |
| $CH_4$ | 33.6 |
| Ne | 49.1 |
| He | 151.3 |
| $H_2$ | 180.5 |

Figure 2:
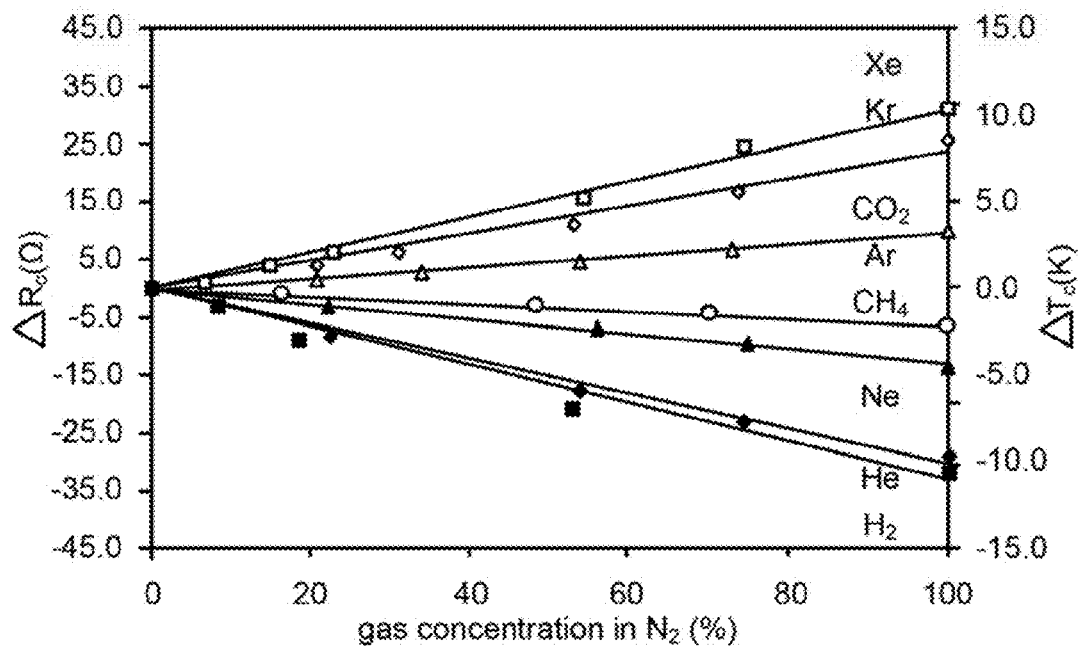
FIG. 2 shows a plot of experimental data showing piezoresistor resistance change and temperature change versus gas percent composition, in one approach.

Using the resistance corresponding to 70 sccm of $N_2$ flow at 298K as a baseline reference, the microcantilever piezoresistance change $\Delta R_c$ versus percent composition for eight binary gas mixtures—$N_2$ with test gases xenon (Xe), krypton (Kr), carbon dioxide ($CO_2$), argon (Ar), methane ($CH_4$), neon (Ne), helium (He), and hydrogen ($H_2$)—was measured experimentally and the data represent averages taken over the eight microcantilever channels, as shown in FIG. 2. The heat dissipation sensor exhibits a linear response to increasing test gas content with respect to the $N_2$ diluent, and achieves a maximum stable value within about one to two minutes. Since $\Delta R_c$ depends on the relative differences in heat dissipation between each gas and $N_2$, those gases with smaller thermal conductivity than $N_2$ cause the embedded piezoresistor to increase in temperature and correspondingly in resistance. Conversely, gases with a larger thermal conductivity lead to a decrease in resistance. These behavioral trends can be observed in FIG. 2.

The microcantilever temperature as a function of gas composition was determined from a resistance versus temperature calibration obtained in a previous study. The operating temperature under the baseline reference condition (70 sccm of $N_2$ flow at 298K) was 311K, with maximum temperature excursions of several Kelvin for the most thermally insulative (Xe, at +8.8K) and conductive ($H_2$, at about 10.1K) pure gases. Note that the operational temperatures for the microcantilever gas sensor are significantly lower than those required for conductometric and catalytic calorimetric detectors (about 500K to about 800K) that are currently available and commonly used in the industry. The temperature changes $\Delta T_c$ versus composition are also shown in FIG. 2 to provide a direct comparison to the corresponding piezoresistance changes. By comparing the magnitudes of $\Delta R_c$ to $\Delta T_c$ as a function of gas composition, it is clear that the heat dissipation mechanism can be a sensitive means of gas detection. For example, an increase in Ar content from 0% to 9.9% for an Ar/N₂ mixture leads to a 170 mK increase in $T_c$ and about a 0.5Ω increase in $R_c$. This change in resistance is readily measured by the Wheatstone circuit, which possesses a noise-limited detection threshold of about 30 mΩ. Applying linear scaling as observed in FIG. 2, the projected limits of detection (LOD) of the current heat dissipation sensor for the test gases is a few parts per thousandth (ppth). These values are comparable to the detection limits of commercial catalytic pellistors, although such sensors can only detect flammable gases below their lower explosive limits and not inert gases such as Ar, which eliminates them from contention in these applications.

If the minimum detectable $\Delta R_c$ could be reduced to less than 1 mΩ, a LOD in the 100 ppm range may be achieved (e.g., 160 ppm of Ar in an N₂ background at 0.8 mΩ resolution). Such a LOD is comparable to that obtained with commercial conductometric sensors, although this detector type is designed for reducing gases and, like catalytic pellistors, is insensitive to inert gases. One strategy that can greatly improve the sensitivity of the thermal conductivity microcantilever sensor is to go from a direct-current (DC) mode of detection, with a steady-state input voltage and output signal amplifier, to an alternating-current (AC) mode using a periodic input voltage and lock-in amplifier. For example, a 20-fold improvement in temperature resolution for piezoresistive microcantilevers using an AC versus DC approach has been reported in the prior art for an optimized measurement frequency of 10 kHz. In addition, a judicious choice of integration time constant with respect to the data sampling rate may also aid in the reduction of noise.

The noise-limited detection threshold (30 mΩ) excludes significant thermal drift effects, since the gas exposure experiments were performed under practically isothermal conditions. From a prior study, in which the microcantilever sensor was operated under ambient outdoor ("field") conditions, it has been observed that environmental temporal temperature gradients of up to about 0.4 mK/s (4K for 3 hrs) during midday sun exposure leading to thermal drift of about 20Ω. Such an effect would easily mask the appearance of a gas to the sensor; for example, a small Ar leak that coincides with a particular drop in temperature. Since the underlying mechanism of detection is thermal in nature (i.e., heat dissipation), any drift compensation method should distinguish the desired $\Delta R_c$ changes due to gas thermal conductivity from those associated with changes in environmental temperature in order to provide accurate detection of gases. A closed-form model, with the ambient temperature as the sole variable input, was used to simulate the thermal drift of a field-deployed piezoresistive microcantilever sensor. Such a model can be readily integrated into the data acquisition software to provide active drift compensation, provided accurate measurements of the gas temperature near the microcantilever are made simultaneously.

Gas detection and identification using dual sensing modalities has also been tested. The inherent ambiguity in the heat dissipation sensor response to various gases can be directly observed by considering the differential responses $\Delta R_c$ versus percent composition shown in FIG. 2. As an illustrative example, a measured response of $\Delta R_c = +5.0\Omega$ could be produced by either 16% Xe, 21% Kr, 51% CO₂, or 56% Ar in N₂; furthermore, any gas mixture with $k < k_{N2}$ will have at least a partial overlap of response, over its full compositional range, with any of these mixture types. The response ambiguity is most striking when the experimental $\Delta R_c$ data averaged over the eight microcantilever channels are displayed in a one-dimensional plot, as in FIG. 3, such that the overlap of the mixture data can be clearly observed. Since thermal conductivity, which underlies the heat dissipation mechanism, is not a unique characteristic of gases, sensor operations which rely solely on this detection approach should be limited to known, specific scenarios—for example, detecting natural gas leaks in an indoor location where no other gas is expected nor probable to be present. If an unexpected gas were present, it might lead to false positives, or potentially mask the presence of the expected gas. For example, a mixture of CO₂ and CH₄ in the proper proportions may lead to a signal indistinguishable from the N₂ baseline reference.

Figure 4:
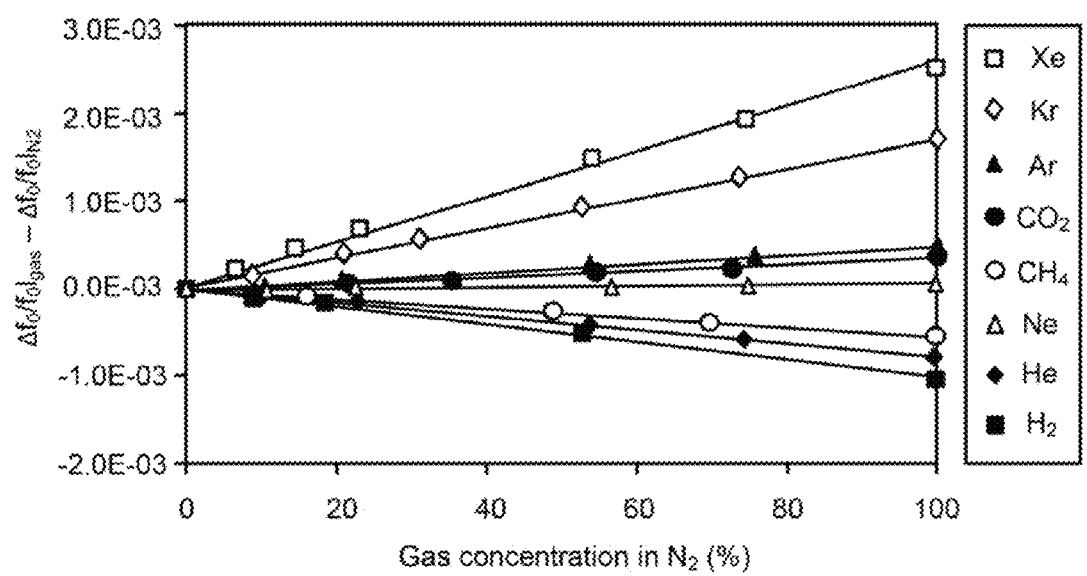
FIG. 4 shows a theoretical plot of a relationship between gases in nitrogen, in one approach.

An additional gas detection method that exploits the microcantilever platform but generates sufficiently orthogonal response data may provide a convenient way to resolve the response ambiguity of a stand-alone thermal sensor. One such method involves measuring the subtle alteration of microcantilever resonant frequency that occurs upon exposure to gases with different viscosities and densities. This method would also suffer from a response ambiguity similar to the thermal case, since these physical properties are also not unique amongst possible gas analytes. However, by utilizing the two sensing modalities in combination, and exploiting their mutual orthogonality through data reduction techniques such as principal components analysis (PCA), a gas sensor with increased discrimination may be obtained, according to various embodiments. The viscous damping of a resonating microcantilever has been previously demonstrated as a viable means of identifying gases. In this study, He, CH₄, N₂, Ar, and CO₂ were detected by measuring shifts in the fundamental frequency with a resolution down to ±0.05%. This resonant method of gas detection relies on a physical principle distinct from the heat dissipation method described previously. Therefore, the data corresponding to each microcantilever-based sensing approach for exposure to the same gases should exhibit at least some degree of mutual orthogonality. Using an expression for shifts of the vacuum fundamental frequency $f_0$ in the viscous damping regime, as shown in Equation 1:

$$\frac{\Delta f_0}{f_0} = \frac{\pi \lambda^a}{3 m_a}\left(\rho + \frac{9}{2\lambda}\sqrt{\frac{\mu \rho}{\pi f_0}}\right) \qquad \text{Equation 1}$$

a data set was simulated for the eight binary mixtures types previously measured by the heat dissipation method. The continuum fluid assumption of the viscous damping regime is appropriate in these cases, since the heat dissipation data were obtained for gases at ambient atmospheric pressure. The density $\rho$ and viscosity $\mu$ of each gas mixture were computed using equations known in the art. The microcantilever mass $m_c$ was estimated as $9 \times 10^{-12}$ kg based on prior art descriptions, and the nominal value of $f_0$ was measured at about 42 kHz. Previous theoretical treatments used contiguous spheres of radius $\lambda$ in a "string of pearls" arrangement to model a viscously damped resonator. For the rectangular microcantilevers used in this work, a value of $\lambda = 13$ μm was obtained by scaling experimentally fitted results for a microcantilever of the same proportional dimensions. A plot of relative frequency shifts ($\Delta f_0/f_0$) versus percent composition in N₂ for the eight analyte mixtures is shown in FIG. 4, where $\Delta f_0/f_0$ for pure N₂ at 760 torr and 298K is used as the reference value. Least squares regression lines are shown for each binary mixture data set. Since N₂ serves as a reference baseline in this study, and Equation 1 represents frequency shifts with respect to the vacuum condition, relative shifts for each gas analyte were obtained by subtracting the value $\Delta f_0/f_0 = 1.30 \times 10^{-3}$ corresponding to an N₂ background at 760 Torr and 298K.

Figure 3:
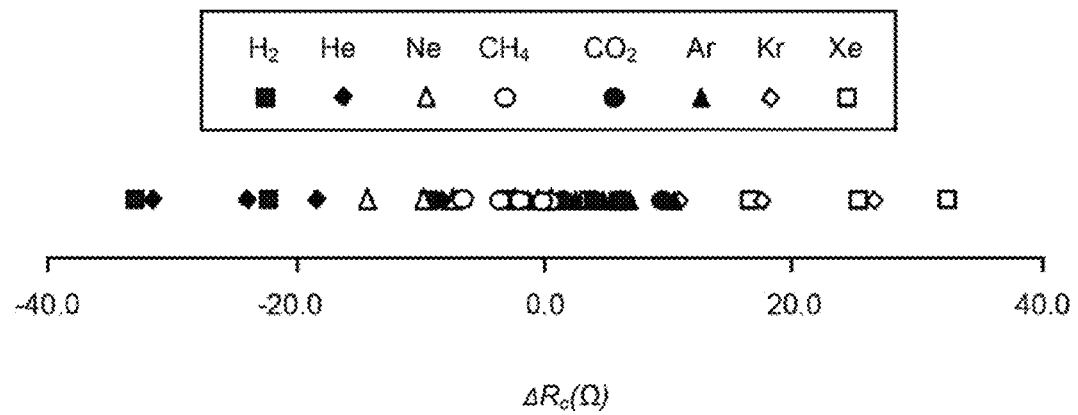
FIG. 3 shows a one-dimensional plot of experimental change in resistance averaged over eight microcantilever channels, in one approach.
Figure 5:
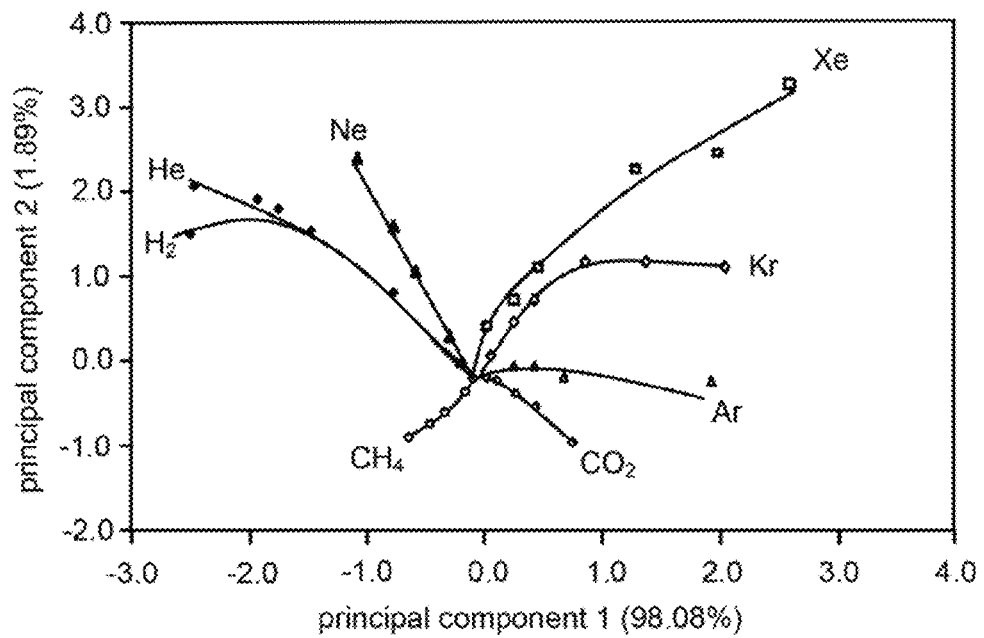
FIG. 5 shows a two-dimensional PCA plot of experimental changes in resistance combined with simulated frequency changes with best fit lines added for example, in one approach.

The experimental $\Delta R_c$ data can be combined with the theoretical relative $\Delta f_0/f_0$ data to represent the response of a hypothetical dual-modality microcantilever sensor. When PCA was applied to this combined data and the two leading components were plotted, vastly improved gas discrimination was observed, as shown in FIG. 5, a two-dimensional PCA plot showing changes in resistance combined with simulated frequency changes with best fit lines added for example, in one approach. The percentages reflect the relative weight each principal component carries in terms of the overall variance in the complete data set (resistance data plus frequency shift data times eight piezoresistive data channels). In FIG. 5, the pure $N_2$ data point is located at (0,0), with increasing gas concentration (up to 100%) toward the more remote data points of each mixture type. Although some ambiguity remains—for example, $He/N_2$ and $H_2/N_2$ are still indistinguishable over most of their compositional range—the improvement over the stand-alone thermal sensor is considerable, as exemplified by the clear distinction between $CH_4$ and $H_2$, which previously overlapped completely, as shown in FIG. 3. Therefore, the combined multimodality data yield more distinct analyte signatures that cannot be obtained from the detection modes individually.

The notion of increasing discrimination using MEMS-based multimodal approaches can be extended beyond microcantilever transducers to an arbitrary number of sensing modes. The integration of multiple transducers and their supporting electronics, using current microfabrication and complementary metal-oxide-semiconductor (CMOS) processes, has been demonstrated in the prior art. Single-chip sensors combining polymer-functionalized microcantilevers, capacitors, and calorimeters for chemical vapor detection have been demonstrated, as well as metal oxide conductometric arrays for gas sensing. Therefore, the single-chip integration of the calorimetric and resonant modes is straightforward using commercially proven technologies, according to some approaches.

In the following descriptions, systems and methods for detecting and identifying one or more gases are shown according to various embodiments.

Figure 6:
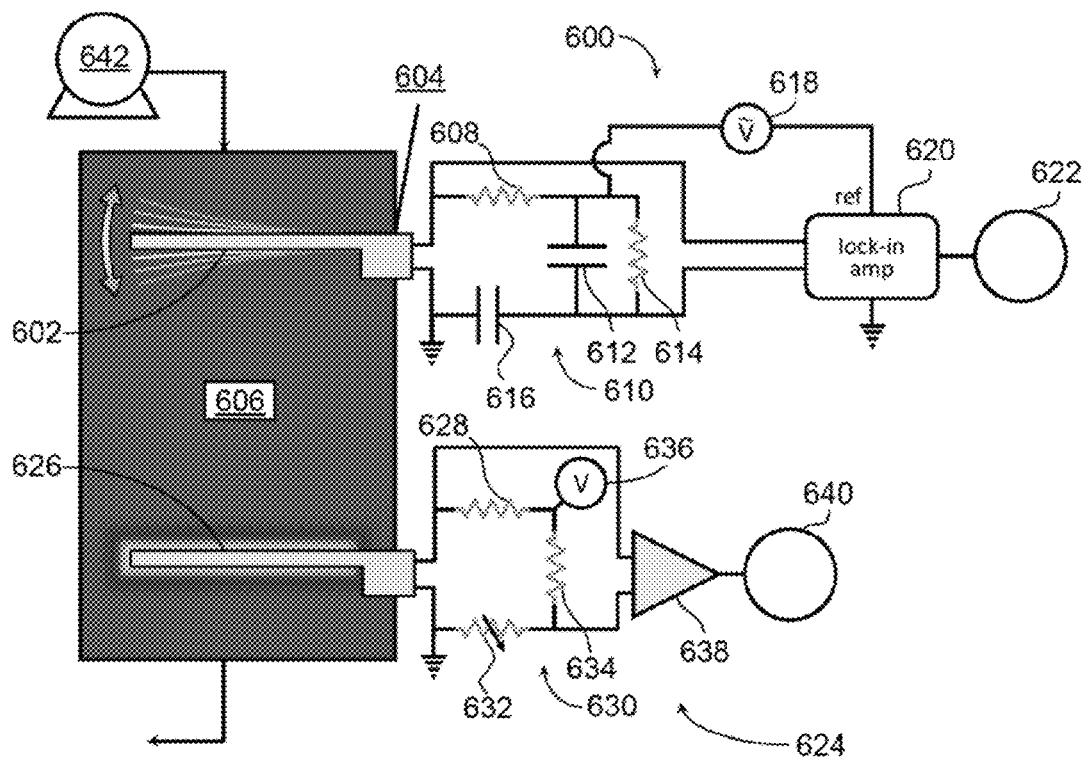
FIG. 6 shows a system for detecting and identifying gases, according to one embodiment.

Now referring to FIG. 6, a system for detecting and identifying gases is shown according to one embodiment. The system includes a subsystem 600 for measuring resonant frequency shifts, and is comprised of a vibrating microcantilever transducer 602, which may include an embedded piezoelectric crystal as an oscillator 604, or any other vibration source as known in the art. Shifts in resonant frequency of the microcantilever 602 are measured, the shifts being due to viscous damping of the microcantilever 602 by the one or more gases 606. The system also includes a subsystem 624 for measuring heat dissipation, and is comprised of a piezoresistive microcantilever transducer 626 containing an embedded piezoresistor. Dissipation of heat from the microcantilever 626 into the one or more gases 606 is measured by changes in the electrical resistance of the piezoresistor. The system also includes a subsystem (not shown, but connected to the output signals 622 and 640) for correlating the measured resonant frequency shifts and resistance changes, respectively, to the one or more gases 606 (e.g., the subsystem identifies if one or more gases are present, and determines the identity of the gases that are present).

According to one embodiment, for each of one or more known gases and corresponding physical properties, the system may be trained to identify these gases by measuring changes in microcantilever electrical resistance and shifts in resonant frequency and compiling this data into a microcantilever electrical resistance and resonant frequency (MERF) profile specific to the particular gas or mixture of gases exhibiting the associated physical property or properties. In this case, the subsystem may comprise a reference database linking one or more gases or physical properties to corresponding MERF profiles, thereby allowing a correlation to be made between observed physical phenomena and a particular gas or gases.

In yet another embodiment, the subsystem may further detect unknown MERF profiles, without being trained as described above, by synthesizing data from one or more gases with known MERF profiles and predicting a novel MERF profile which accounts for the observed physical phenomena.

In any of the above embodiments, the reference database may be any suitable type of analytical tool as known in the art, such as mathematical equations, graphical representations, lookup tables, software algorithms, etc., for computing gas identity from at least electrical resistance and resonant frequency data.

According to one embodiment, the microcantilever transducers may be constructed of a material comprising silicon, e.g., silicon, a silicon-based compound, a silicon resin, etc.

In one embodiment, the vibrating microcantilever transducer 600 may be wired serially to a surface mounted resistor 608 to form a first voltage divider leg of an alternating-current (AC) bridge circuit 610. In a further embodiment, the system may include a first surface mounted capacitor 612 wired in parallel to a second surface mounted resistor 614, which together may be wired serially to a second surface mounted capacitor 616 to form a second voltage divider leg of the AC bridge circuit 610. Additionally, an AC voltage source 618 may be applied to the first and second voltage divider legs of the AC bridge circuit 610 to drive the circuit, thereby allowing the circuit to function. In this case, the bridge voltage is measured using a lock-in amplifier 620 coupled to a midpoint of the first and second voltage divider legs, and the output signal 622 may be recorded in the form of resonant frequency shifts $\Delta f_0/f_0$.

In another embodiment, the piezoresistive microcantilever transducer 626 may be wired serially to a first surface mounted resistor 628 to form a first voltage divider leg of a Wheatstone bridge circuit 630. In a further embodiment, the system may include a potentiometer 632 wired serially to a second surface mounted resistor 634 to form a second voltage divider leg of the Wheatstone bridge circuit 630. In addition, a direct-current (DC) voltage source 636 may be applied to the first and second voltage divider legs of the Wheatstone bridge circuit 630 to drive the circuit, thereby allowing the circuit to function. In this case, the bridge voltage is measured using a differential amplifier 638 coupled to a midpoint of the first and second voltage divider legs, and the output signal 640 may be recorded in the form of voltage changes $\Delta V$ correlated to the resistance changes in the piezoresistor.

In one embodiment, the direct current resulting from the DC voltage source 636 applied to the first and second voltage divider legs may be substantially constant.

In another embodiment, the DC bridge circuit 630 in the subsystem 624 may be replaced with an AC bridge circuit similar to the circuit 610 in the subsystem 600, which may allow improvements in the signal-to-noise characteristics of the output 640.

In any of the above described embodiments, the system may further include a hermetically sealed enclosure. This enclosure may house (when provided in the system): the first surface mounted resistor 608, the second surface mounted resistor 614, the first surface mounted capacitor 612, and the second surface mounted capacitor 616 in the subsystem 600; the first surface mounted resistor 628, the second surface mounted resistor 634, the potentiometer 632, and the differential amplifier 638 in the subsystem 624.

According to one approach, the temperature coefficient of resistance of the piezoresistor in the piezoresistive microcantilever 626 may be about 30 to 60 times as great as temperature coefficients of resistance of the first surface mounted resistor 628, the second surface mounted resistor 634, and the potentiometer 632.

In another approach, the system may include a low compression ratio pump 642 that maintains a substantially constant flow rate of the one or more gases 606 of about 10 standard cubic centimeters per minute (sccm).

In any of the above embodiments, the system may be calibrated against a known gas or gas mixture, for example argon and/or ambient air, to establish a baseline environmental gas composition against which experimental data may be compared to detect changes to the baseline environmental gas composition, in some approaches.

In one embodiment, the piezoresistive microcantilever transducer 626 and the vibrating microcantilever transducer 600 may be integrated with each other, e.g., they may be a single microcantilever which can operate as a piezoresistive microcantilever and as a vibrating microcantilever.

In any of the above embodiments, alternative and/or additional sample properties may be of interest, for example: pressure, temperature, flow-rate, etc., may be of broad interest in scientific and commercial applications. Sensors employing mechanical, thermal, and/or other detection mechanisms may be utilized singularly or in combination to measure alternative or additional sample properties mentioned herein.

Figure 7:
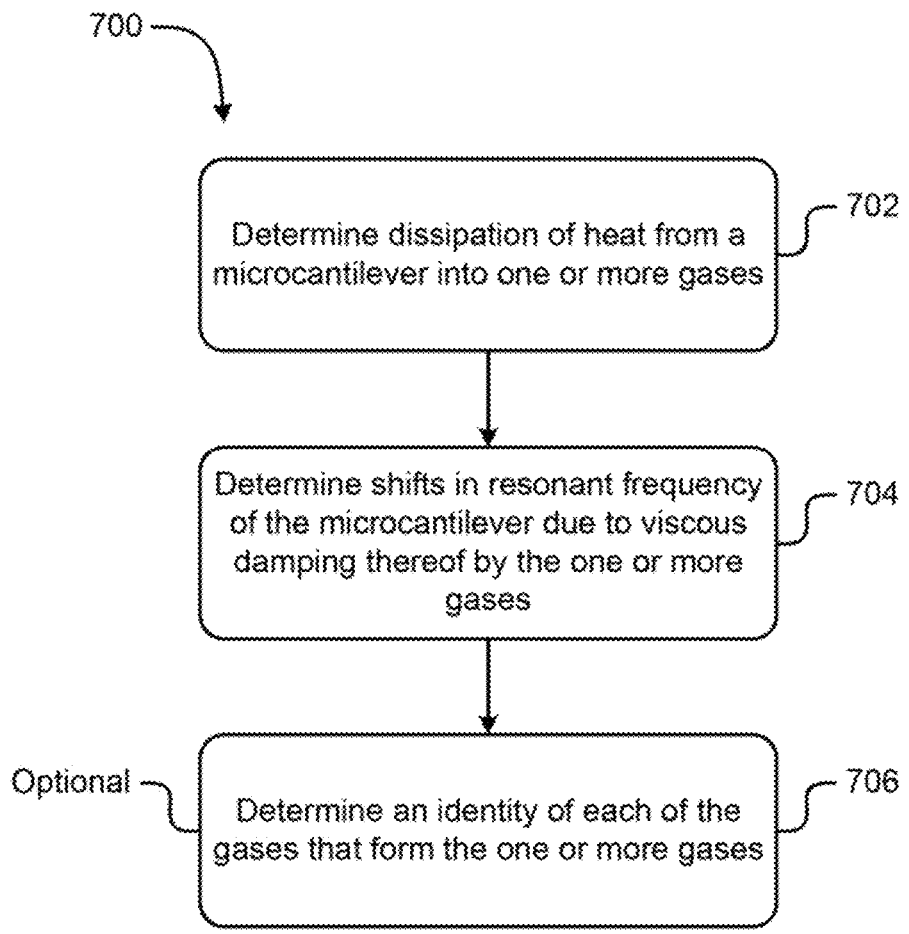
FIG. 7 is a flowchart of a method, according to one embodiment.

Now referring to FIG. 7, a method 700 for detecting and identifying one or more gases is described in a simplified flowchart. The method 700 may be carried out in any desired environment, and may include and/or make use of any of the embodiments and approaches described herein.

In operation 702, the dissipation of heat from a microcantilever into one or more gases is determined. Any apparatus, method, or technique may be used to determine the dissipation, and the microcantilever need not be vibrating during this determination, as would be known to one of skill in the art.

In one approach, the dissipation of heat from the microcantilever into the one or more gases may be determined using a microcantilever transducer having an embedded electrically powered piezoresistor (such as those described herein). This determination may be carried out by measuring changes in the electrical resistance of the piezoresistor.

In operation 704, shifts in resonant frequency of the microcantilever due to viscous damping thereof by the one or more gases is determined. Any apparatus, method, or technique may be used to determine the shifts, as would be known to one of skill in the art.

In one approach, the shifts in resonant frequency of the microcantilever due to viscous damping thereof by the one or more gases may be determined by measuring shifts in resonant frequency of the microcantilever while the microcantilever is vibrating.

In optional operation 706, the identity of each of the gases that form the one or more gases is determined. The identity of each gas may be determined through any method, and particularly by predetermining a mapping for each gas and gas mixture, then selecting a best fit mapping to the information determined through operations 702 and 704.

In one approach, the microcantilever may be constructed of a material comprising silicon, e.g., silicon, a silicon-based compound, a silicon resin, etc.

Of course, one microcantilever or multiple microcantilevers may be used to determine shifts in resonant frequency and dissipation of heat, according to various embodiments. For example, two microcantilevers may be used to determine shifts in resonant frequency, one primary and one for backup, and two microcantilevers may be used to dissipation of heat, one primary and one for backup. Many other arrangements may also be possible as would be known by one of skill in the art.

A computer program product for detecting and identifying one or more gases, according to one embodiment, includes a computer readable medium having computer readable program code embedded therein. This computer program product may be used in conjunction with any of the systems and/or methods described herein. Particularly, information obtained through use of a microcantilever transducer regarding heat dissipation into and viscous damping of one or more gases may be used to detect and identify one or more gases.

In one embodiment, the computer readable program code is configured to: receive data regarding changes in the electrical resistance of a piezoresistor; receive data regarding shifts in a resonant frequency of a microcantilever; determine the dissipation of heat from the microcantilever into one or more gases based on the data regarding changes in the electrical resistance of a piezoresistor; determine viscous damping of the one or more gases based on the data regarding shifts in a resonant frequency of a microcantilever; correlate the dissipation of heat and the viscous damping to one or more gases; and output the identity of the one or more gases based on the correlation.

Outputting may include printing, displaying, copying, transferring, sending, etc., the results of the gas detection and identification, according to various embodiments.

Figure 8:
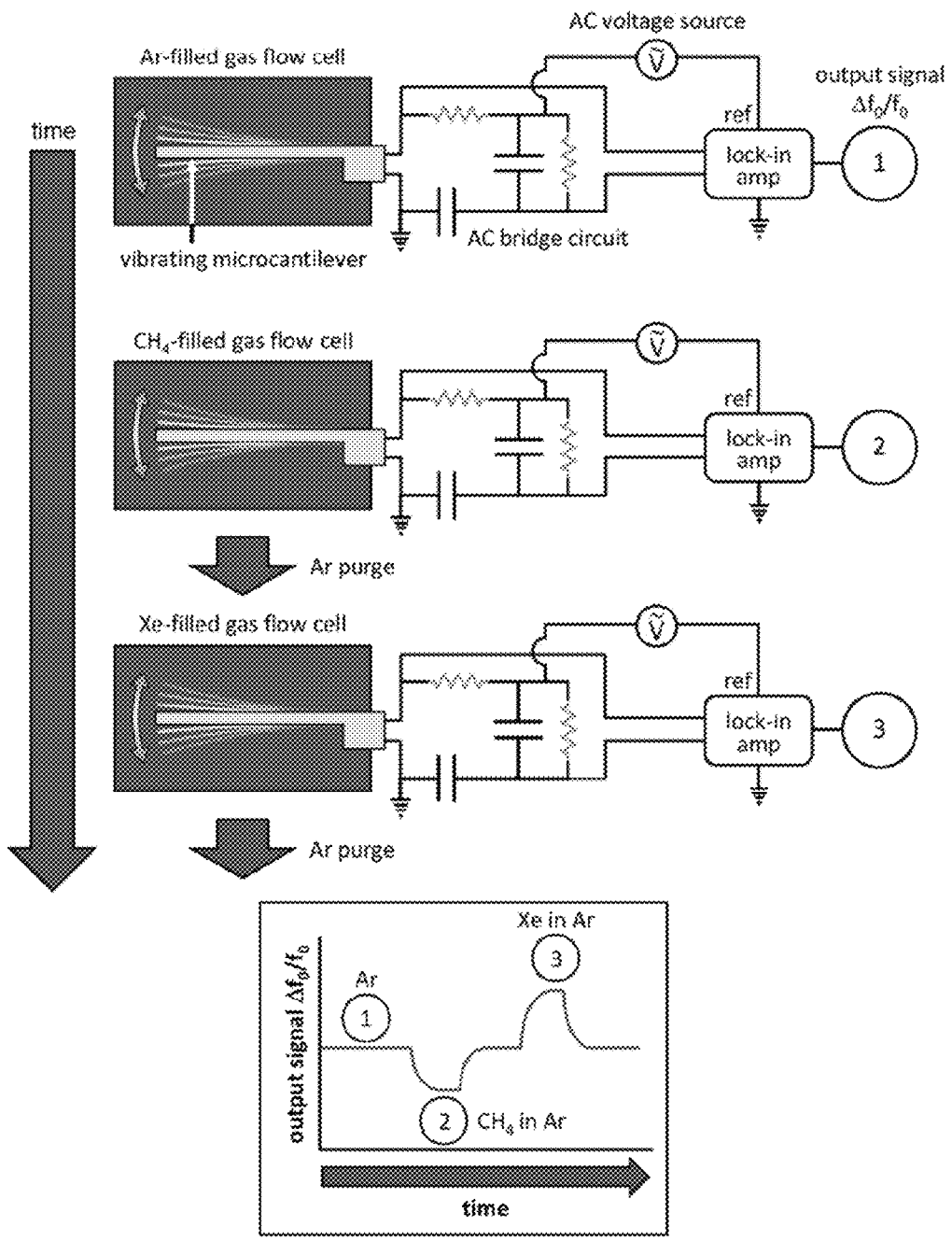
FIG. 8 shows a system for detecting and identifying gases using a resonant frequency of a microcantilever, and the possible output therefrom, according to one embodiment.

Now referring to FIG. 8, an illustrative embodiment is shown of a system for detecting and identifying gases using the resonant frequency of a microcantilever, and the possible output therefrom. As can be seen in the plot, the output signal ($\Delta f_0/f_0$) changes based on the gas which is present in the flow cell. The outputs for each gas are designated by a number which denotes a point in time when a certain gas is present in a steady state condition: 1 for Ar, 2 for $CH_4$, and 3 for Xe. The plot shows that the output signal for $CH_4$ at time point 2 is lower than the output signal for Ar, which serves as a reference baseline in this example. The relative reduction in frequency shift is the result of the reduced viscosity and density of $CH_4$ compared to Ar. As the $CH_4$ is purged from the gas flow cell by Ar, the output signal returns to the value at time point 1. At time point 3, Xe is introduced into the gas flow cell, and the output signal for Xe is higher than the output signal for Ar. The relative increase in frequency shift is the result of the increased viscosity and density of Xe compared to Ar. As the Xe is purged from the gas flow cell by Ar, the output signal returns again to the value at time point 1. The relative magnitudes of the output signal changes at 2 and 3 is described by Equation 1.

Figure 9:
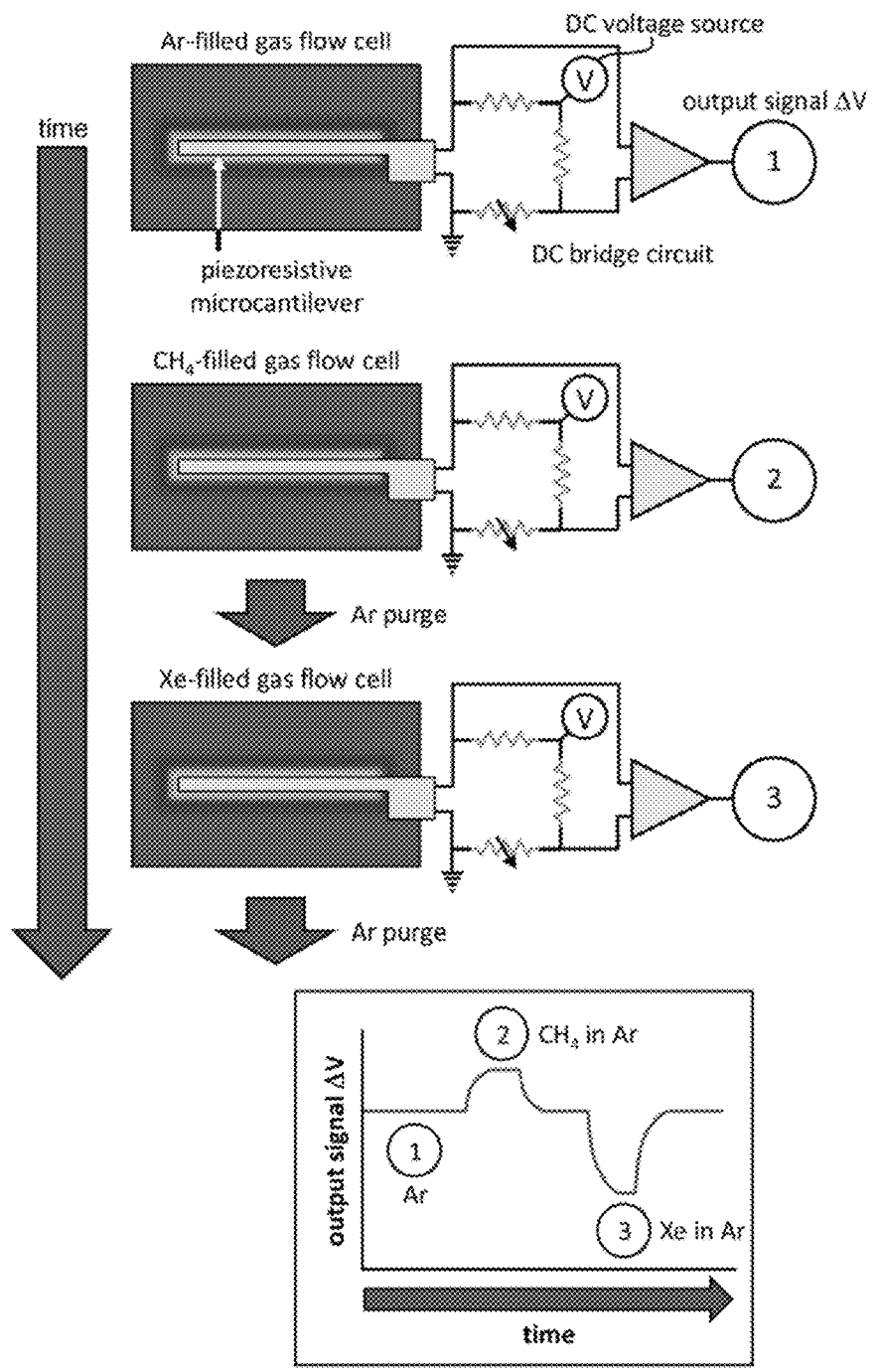
FIG. 9 shows a system for detecting and identifying gases using electrical resistance of a piezoresistor, and the possible output therefrom, according to one embodiment.

Now referring to FIG. 9, an illustrative embodiment is shown of a system for detecting and identifying gases using the electrical resistance of a piezoresistor, and the possible output therefrom. As can be seen in the plot, the output signal ($\Delta V$) changes based on the gas which is present in the flow cell. The outputs for each gas are designated by a number which denotes a point in time when a certain gas is present in a steady state condition: 1 for Ar, 2 for $CH_4$, and 3 for Xe. The plot shows that the output signal for $CH_4$ at time point 2 is higher than the output signal for Ar, which serves as a reference baseline in this example. The relative increase in $\Delta V$, which is directly correlated to the resistance of the piezoresistor, is the result of the increased thermal conductivity of $CH_4$ compared to Ar. As the $CH_4$ is purged from the gas flow cell by Ar, the output signal returns to the value at time point 1. At time point 3, Xe is introduced into the gas flow cell, and the output signal for Xe is lower than the output signal for Ar. The relative decrease in $\Delta V$, which is directly correlated to the resistance of the piezoresistor, is the result of the decreased thermal conductivity of Xe compared to Ar. As the Xe is purged from the gas flow cell by Ar, the output signal returns again to the value at time point 1.

These two illustrative embodiments, and the experimental and theoretical results described previously, show that the output signals from each detection method are substantially different as a result of the differences in the fundamental physical principles upon which each method is based. As demonstrated previously, the combination of the output signals from each of these detection methods provides vastly improved gas discrimination compared to each detection method individually.

According to various embodiments, the gas sensors and gas sensing methods described herein may be used for gas sensing applications such as the detection of combustible gases (e.g., low molecular weight hydrocarbons like methane, ethane, butane, etc.) below the lower explosive limit in certain confined areas, such as coal mines, enclosed landfill sites, conveyances for flight and underwater travel (e.g., airplanes, space shuttles, submarines, etc.), structures having confined areas (e.g., hospitals, factories, etc.), the petrochemical industry (oil rig platforms, etc.), etc. Other applications include environmental monitoring of air pollutants such as carbon dioxide, nitric oxide, sulfur dioxide, etc. More applications include distributed sensors related to hydrogen fuel cell technology (e.g., potential future hydrogen supply infrastructure, including monitoring, safety, etc.). Also, some more specialized applications include those involving inert gases (e.g., helium, xenon, etc.) that are undetectable by current commercial off-the-shelf sensors.

While various embodiments have been described above, it should be understood that they have been presented by way of example only, and not limitation. Thus, the breadth and scope of a preferred embodiment should not be limited by any of the above-described exemplary embodiments, but should be defined only in accordance with the following claims and their equivalents.

What is claimed is:

1. A system for detecting and identifying gases, the system comprising:
   a piezoresistive microcantilever transducer, wherein dissipation of heat from the piezoresistive microcantilever into one or more gases is measured by changes in an electrical resistance of the piezoresistor;
   a vibrating microcantilever transducer, wherein shifts are measured in resonant frequency of the vibrating microcantilever due to viscous damping thereof by the one or more gases; and
   a subsystem for correlating the measured resistance changes and the resonant frequency shifts to the one or more gases.

2. The system of claim 1, wherein the two microcantilever transducers are constructed of a material comprising silicon.

3. The system of claim 1, further comprising a hermetically sealed enclosure, wherein the hermetically sealed enclosure protects portions of the system from environmental interference.

4. The system of claim 1, further comprising a low compression ratio pump that maintains a substantially constant flow rate of the one or more gases of about 10 standard cubic centimeters per minute (sccm).

5. The system of claim 1, wherein a single microcantilever comprises the piezoresistive microcantilever transducer and the vibrating microcantilever transducer.

6. The system of claim 1, further comprising a plurality of parallel gas flow circuits.

7. The system of claim 1, wherein the one or more gases comprise at least one gas selected from a group consisting of: nitrogen, hydrogen, methane, carbon dioxide, helium, neon, xenon, krypton, and argon.

8. The system of claim 1, wherein the one or more gases comprise nitrogen and at least one gas selected from a group consisting of: hydrogen, methane, carbon dioxide, helium, neon, xenon, krypton, and argon.

9. The system of claim 1, wherein the subsystem is further configured to detect unknown microcantilever electrical resistance and resonant frequency (MERF) profiles without any training.

10. The system of claim 1, wherein the vibrating microcantilever transducer is part of a second subsystem configured to measure resonant frequency shifts, the second subsystem further comprising:
    a piezoelectric crystal embedded in the piezoresistive microcantilever;
    an alternating-current (AC) bridge circuit comprising:
        a first surface mounted resistor coupled to the vibrating microcantilever transducer;
        a first surface mounted capacitor coupled to a second surface mounted resistor; and
        a second surface mounted capacitor coupled to the first mounted capacitor and the second surface mounted resistor; and
    an AC voltage source,
    wherein the piezoresistive microcantilever transducer is part of a third subsystem configured to the dissipation of heat from the piezoresistive microcantilever into one or more gases, the third subsystem further comprising:
        a direct-current (DC) circuit comprising:
            a first surface-mounted resistor coupled to the piezoresistive microcantilever transducer;
            a potentiometer coupled to a second surface mounted resistor; and
            a DC voltage source coupled to the first surface mounted resistor and the second surface mounted resistor; and
        a differential amplifier.

11. The system of claim 1, further comprising a reference database coupled to the subsystem, the reference database linking at least one of:
    one or more gases to one or more corresponding MERF profiles; and
    one or more physical properties to one or more corresponding MERF profiles.

12. A method for detecting and identifying one or more gases, the method comprising:
    determining dissipation of heat from a microcantilever into one or more gases using one or more sensors;
    determining shifts in resonant frequency of the microcantilever using the one or more sensors, the shifts in resonant frequency being due to viscous damping of the microcantilever by the one or more gases; and
    determining an identity of each of the one or more gases based on both 1) the dissipation of heat from the microcantilever, and 2) the shifts in the resonant frequency of the microcantilever.

13. The method of claim 12, wherein the dissipation of heat from the microcantilever is determined based on changes in an electrical resistance of a piezoresistor coupled to the microcantilever, wherein the microcantilever is constructed of a material comprising silicon.

14. The method of claim 12, wherein dissipation of heat from a microcantilever into the one or more gases is determined using a microcantilever transducer having an embedded electrically powered piezoresistor by measuring changes in an electrical resistance of the piezoresistor.

15. The method of claim 12, wherein shifts in a resonant frequency of the microcantilever due to viscous damping thereof by the one or more gases is determined by measuring shifts in resonant frequency of the microcantilever while the microcantilever is vibrating.

16. The method of claim 12, wherein the microcantilever is constructed of a material comprising silicon.

17. The method of claim 12, wherein the same microcantilever is used for the determination of the dissipation of heat from the microcantilever into the one or more gases and for the determination of the shifts in the resonant frequency of the microcantilever due to viscous damping thereof by the one or more gases.

18. The method of claim 12, further comprising determining one or more unknown microcantilever electrical resistance and resonant frequency (MERF) profiles specific to one or more particular gases or gas mixtures.

19. A computer program product for detecting and identifying one or more gases, the computer program product comprising:
a non-transitory computer readable medium having computer readable program code embedded therein, the computer readable program code configured to:
receive data regarding changes in an electrical resistance of a piezoresistor;
receive data regarding shifts in resonant frequency of a microcantilever;
determine dissipation of heat from the microcantilever into one or more gases based on the data regarding changes in the electrical resistance of the piezoresistor;
determine viscous damping of the one or more gases based on the data regarding shifts in resonant frequency of the microcantilever;
correlate the dissipation of heat and the viscous damping to one or more gases; and
output the identity of the one or more gases based on the correlation.

20. The computer program product of claim 19, wherein the computer readable program code is further configured to synthesize data from one or more gases having known microcantilever electrical resistance and resonant frequency (MERF) profile(s) to predict a novel MERF profile.

* * * * *